United States Patent [19]

Felix

[11] Patent Number: 4,569,802

[45] Date of Patent: Feb. 11, 1986

[54] METHOD FOR PREPARATION OF N-PHOSPHONOMETHYLGLYCINE

[75] Inventor: Raymond A. Felix, Richmond, Calif.

[73] Assignee: Stauffer Chemical Company, Westport, Conn.

[21] Appl. No.: 507,813

[22] Filed: Jun. 27, 1983

[51] Int. Cl.$^4$ ............................................. C07F 9/38
[52] U.S. Cl. .............................. 260/502.5 F; 260/944
[58] Field of Search ................................... 260/502.5 E

[56] References Cited

PUBLICATIONS

Wagner et al., "Synthetic Organic Chemistry", (1953) pp. 92, 666–667, 678–679, and 416.

Kosolapoff, "Organophosphorus Compounds" (1950) pp. 121–124, and 139.

Primary Examiner—Anton H. Sutto
Attorney, Agent, or Firm—Paul R. Martin; Edwin H. Baker

[57] ABSTRACT

A method of preparing N-phosphonomethylglycine comprising; (a) reacting N-hydroxymethyl haloacetamide with a chlorinating agent, preferably thionyl chloride to form N-chloromethyl haloacetamide; (b) reacting N-chloromethyl haloacetamide with a phosphite to form N-haloacetylaminomethyl phosphonate; (c) reacting the phosphonate with derivative of haloacetic acid to form N-haloacyl-N-(cyanomethyl or carboalkoxymethyl) phosphonate; and (d) hydrolyzing this later phosphonate to yield N-phosphonomethylglycine.

9 Claims, No Drawings

METHOD FOR PREPARATION OF N-PHOSPHONOMETHYLGLYCINE

FIELD OF THE INVENTION

This invention is a new process for preparing N-phosphonomethylglycine.

BACKGROUND OF THE INVENTION

Certain salts of N-phosphonomethylglycine are effective as post-emergence herbicides. A commercial herbicide contains the isopropylamine salt of N-phosphonomethylglycine.

N-Phosphonomethylglycine can be made by a number of methods. One such method, as described in U.S. Pat. No. 3,160,632 is to react N-phosphinomethylglycine(glycinemethylenephosphonic acid) with mercuric chloride in water at reflux temperature, and subsequently separating the reaction products. Other methods are phosphonomethylation of glycine and the reaction of ethyl glycinate with formaldehyde and diethylphosphite. The latter method is described in U.S. Pat. No. 3,799,758. In addition, there is a series of patents relating to the preparation of N-phosphonomethylglycine, including U.S. Pat. Nos. 3,868,407, 4,197,254 and 4,199,354.

Close prior art is U.S. Pat. No. 3,923,877, which teaches the reaction of 1,3,5-tricyanomethylhexahydro-1,3,5-triazine with excess disubstituted phosphite to form $(RO)_2P(O)CH_2NHCH_2CN$ (R is hydrocarbyl or substituted hydrocarbyl) which is hydrolyzed to yield N-phosphonomethylglycine.

Because of the commercial importance of N-phosphonomethylglycine salts as herbicides, improved methods of preparing N-phosphonomethylglycine are valuable.

BRIEF DESCRIPTION OF THE INVENTION

This invention relates to a process for preparing N-phosphonomethylglycine which comprises:

(a) reacting N-hydroxymethyl haloacetamide with a chlorinating agent, preferably thionyl chloride to form N-chloromethyl haloacetamide;

(b) reacting N-chloromethyl haloacetamide with a phosphite to form N-haloacetylaminomethyl phosphonate;

(c) reacting the phosphonate with a derivative of halo acetic acid to form N-haloacylmethyl-N-(cyanomethyl or carboalkoxymethyl)aminomethyl phosphonate; and (d) hydrolyzing this later phosphonate to yield N-phosphonomethylglycine.

DETAILED DESCRIPTION OF THE INVENTION

The process of this invention may be illustrated by the following reaction scheme:

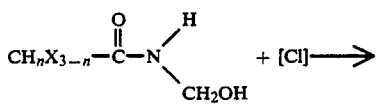

(a)

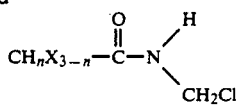

wherein [Cl] is a chlorinating agent such as thionyl chloride, phosgene, hydrogen chloride, phosphorus trichloride, phosphorus oxychloride and the like; X is chlorine, bromine, or fluorine, preferably fluorine and n is the integer 0 or 1.

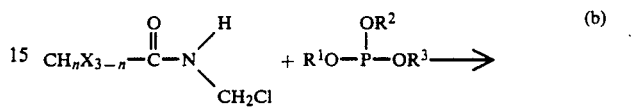

(b)

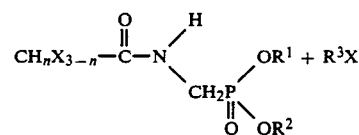

wherein n and X are defined as above and $R^1$ and $R^2$ are both aromatic groups or both aliphatic group, preferably $R^1$ and $R^2$ are $C_1$-$C_6$ alkyl, more preferably $C_1$-$C_4$ alkyl, and $R^3$ is an aliphatic group, preferably $R^3$ is $C_1$-$C_6$ alkyl, more preferably $C_1$-$C_4$ alkyl or $R^3$ is an alkali metal (M), preferably sodium or potassium.

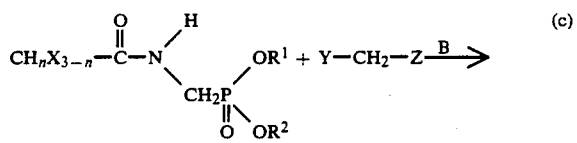

(c)

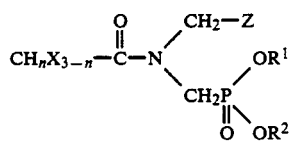

wherein Y is chlorine, bromine or iodine, preferably chlorine, Z is cyano or

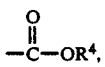

n, X, $R^1$, and $R^2$ are as defined and $R^4$ is an aromatic or aliphatic group, preferably $C_1$-$C_6$ alkyl, more preferably $C_1$-$C_4$ alkyl and B is a non-nucleophilic base.

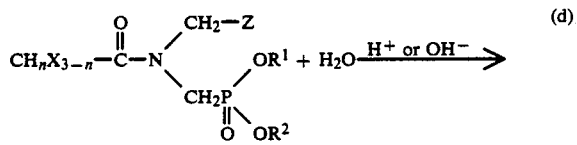

(d)

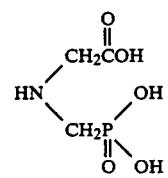

wherein X, n, $R^1$, $R^2$ and Z are as defined above and $H^+$ is a strong acid such as hydrochloric, hydrobromic, hydriodic, nitric, sulfuric, phosphonic or chloroacetic acid. Preferably $H^+$ is hydrochloric or hydrobromic acid and $OH^-$ is a strong base such as sodium hydroxide or potassium hydroxide, preferably in an aqueous, aqueous-alcoholic or alcoholic solution. Preferably, the hydroylsis is run in the presence of a strong acid.

In the above reaction scheme the groups $R^1$ or $R^2$ are not directly involved in reaction step (b) between the N-chloromethyl haloacetamide reaction product of step (a) and the phosphite. Groups $R^1$ and $R^2$ are removed in reaction step (d) when the phosphonate reaction product of reaction step (c) is subjected to hydrolysis. Therefore, the nature of groups $R^1$ and $R^2$ is not critical, although groups which would interfere with reaction steps (a), (b), (c) and (d) are to be avoided.

The group "$C_1$-$C_4$ alkyl" encompasses methyl, ethyl, n-propyl, isopropyl, n-butyl, isobutyl, sec-butyl, and tert-butyl. The group "$C_1$-$C_6$ alkyl" encompasses the same radicals as $C_1$-$C_4$ alkyl plus the 6 pentyls and the 16 hexyls.

The term "aliphatic group" is used in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

Reaction step (a) preferably is run at a temperature between about 0° to about 150° C., more preferably between about 40° to about 110° C. and most preferably between about 75° to about 85° C. This reaction step can be run at atmospheric, sub-atmospheric or super-atmospheric pressure, preferably at atmospheric pressure. Preferably the reaction is run in a solvent for the amide, such as ethylene dichloride, methylene chloride, tetrahydrofuran or toluene.

One mole of the chlorinating agent is needed to react with one mole of the N-hydroxymethyl haloacetamide. Preferably, an excess of chlorinating agent is used to insure complete reaction with the haloacetamide. The N-chloromethyl haloacetamide reaction products of step (a) are available or can be easily prepared by other known procedures. Therefore, the process of this invention need not include step (a) and thus can start at step (b).

Most preferably no excess chlorinating agent is used and the solvent used in reacton step (a) is also used as the solvent in reaction step (b). Thus, no solvent need be removed after completion of step (a) and it is used in reaction step (b). However, if a higher boiling solvent is desired in step (b), the solvent used in step (a) can be removed by vacuum distillation.

In reaction step (b), most preferably about equal mole amounts of the N-chloromethyl haloacetamide and the phosphite are reacted. Less preferably, up to 2 mole excess can be used and least preferably up to a 10 mole excess can be used.

The reaction is exothermic and can be run at a temperature between about 0° to about 150° C., more preferably between about 40° to about 100° C.; most preferably between 75° to about 85° C.

No solvent is needed for the reaction, however, any inert solvent can be used, preferably the solvent having a boiling point between about 40° to about 110° C. Examples of such solvents are ethylene chloride, methylene chloride, tetrahydrofuran and toluene. The use of an inert solvent helps dissipate the heat of reaction. Most preferably the solvent is the one used in reaction step (a). Any solvent used in this reaction step will be removed after completion of reaction step (c), so preferably it is one that can be removed by evaporation.

Alkali metal phosphites having the formula

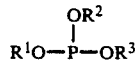

wherein $R^1$ and $R^2$ are as defined and $R^3$ is an alkali metal are reacted with N-halomethyl haloacetamide under an inert atmosphere such as nitrogen. The alkali metal phosphite can be prepared by reacting an alkali metal alkoxide, alkali metal hydride or alkali metal with an equal mole amount of a disubstitued phosphite of the formula

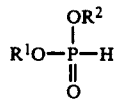

wherein $R^1$ and $R^2$ are as defined. This reaction is run in an inert atmosphere such as nitrogen.

Alkali metal phosphites of the formula

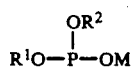

where $R^1$, $R^2$ and M are as defined can, because of tautomerism, have the following additional structural formula

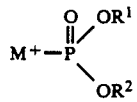

wherein $R^1$ and $R^2$ are as defined and M is an alkali metal.

Reaction step (c) is preferably run at a temperature between about 0° C. to about 150° C., more preferably between about 25° to about 60° C. This reaction step can be run at atmospheric, sub-atmospheric, or superatmospheric pressure, preferably at atmospheric pressure. Preferably the reaction is run in a polar solvent, such as acetone, methylethyl ketone, dimethylformamide or tetrahydrofuran. One mole of the carboalkoxy or cyanide compound is needed to react with one mole of the phosphonate; furthermore, an excess of the carboalkoxy or cyanide compound can be used to insure complete reaction with the phosphonate. The non-nucleophilic bases should be compatible with the solvent used, i.e., it should not react with the solvent selected. Examples of non-nucleophilic bases are potassium carbonate, sodium hydride, and hindered potassium alkoxides such as potassium t-butoxide. Nucleophilic bases such as sodium hydroxide, potassium hydroxide, triethylamine, and pyridine are not preferred. The solvent, or any excess carboalkoxy or cyanide compound can be removed to isolate the O,O-dialkyl-N-(carboalkoxymethyl or cyanomethyl)-N-haloacetylaminomethyl phosphonate.

In reaction step (d), a mole of the phosphonate reaction product from reaction step (c) is hydrolyzed with 5 moles of water. The hydrolysis is run in the presence of a strong acid or base as defined above. Preferably the hydrolysis is acid-catalyzed, preferably with an inorganic acid, and most preferably with hydrochloric or hydrobromic acid. The hydrolysis yields the desired N-phosphonomethylglycine. Preferably at least 2 moles of the acid are used. More preferably, a large excess over the 2 mole amount is used. The preferred hydrochloric or hydrobromic acid can be used in concentrated or aqueous form.

This last reaction step is run at a temperature between about 0° to about 200° C., preferably between about 50° to about 125° C. and most preferably between about 100° to about 125° C.

Atmospheric, sub-atmospheric or super-atmospheric pressure can be used. Preferably atmospheric pressure is used during the hydrolysis.

The solid N-phosphonomethylglycine can be recovered by conventional techniques in reaction step (d). Volatile liquid products such as alcohols (methanol) chlorides (methyl chloride), acids (haloacetic acid), water, and excess acid can be removed by standard stripping techniques. The desired N-phosphonomethylglycine is recovered in high purity by dissolving it in water, adjusting the pH of the solution to between 1 and 2, allowing it to crystallize from solution and removing it by filtration.

The process of this invention can be better understood by reference to the following specific examples.

EXAMPLE 1

Preparation of N-chloromethyl trifluoroacetamide

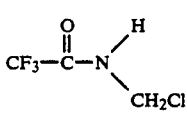

51.7 grams (g) (0.36 mole) of N-hydroxymethyl trifluoroacetamide were dissolved in 350 milliliters (ml) dichloromethane in a round-bottom flask equipped with a magnetic stirrer and reflux condenser. Thirty-three ml (0.45 mole) thionyl chloride were added dropwise with vigorous stirring. The reaction mixture was heated at reflux until the gas evolution ceased. The resulting mixture was then stripped under reduced pressure to yield the desired product.

EXAMPLE 2

Preparation of O,O-diethyl-N-trifluoromethylaminomethyl phosphonate

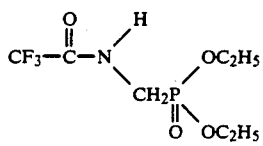

The reaction product of Example I was dissolved in 70 ml toluene. Sixty-two ml (0.362 mole) triethylphosphite was added dropwise with stirring. When the exothermic reaction ceased the resulting mixture was stripped under reduced pressure to yield the desired product. Structure was confirmed by infrared, proton nuclear magnetic resonance, and mass spectroscopy.

EXAMPLE 3

Preparation of O,O-diethyl-N-carbomethoxymethyl-N-trifluoroacetylaminomethyl phosphonate

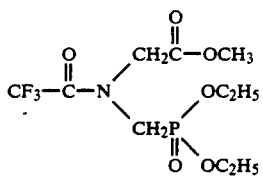

Five g (0.019 mole) of O,O-diethyl-N-trifluoroacetylaminomethylphosphonate, 2.8 g (0.02 mole) of powdered potassium carbonate, 0.33 g (0.002 mole) of powdered potassium iodide, 15 ml of acetone, and 2.12 g (0.0196 mole) of methyl chloroacetate were combined in a round bottom flask and heated to reflux for one hour with mechanical stirring. The reaction mixture was then stripped under reduced pressure, extracted with dichloromethane, decanted and stripped under reduced pressure to yield the desired product. Structure was confirmed by infrared, proton nuclear magnetic resonance and mass spectroscopy.

EXAMPLE 4

Preparation of N-phosphonomethylglycine

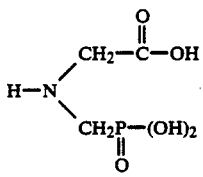

The phosphonate reaction product of Example 3 (5.3 g, 0.0158 mole) was combined with 25 ml (0.30 mole) of concentrated hydrochloric acid, refluxed 1.5 hours, and stripped under reduced pressure. Structure was confirmed by ir, nmr, and liquid chromatograph (lc).

EXAMPLE 5

Preparation of
O,O-diethyl-N-cyanomethyl-N-tri-
fluoroacetylaminomethyl phosphonate

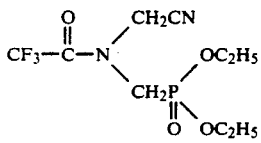

13.2 g (0.05 mole) of O,O-diethyl-N-tri-fluoroacetylaminomethyl phosphonate, 7.18 g (0.052 mole) of powdered potassium carbonate, 0.86 g (0.0052 mole) of powdered potassium iodide, 40 ml acetone and 3.26 ml (0.052 mole) of chloroacetonitrile were combined in a round-bottom flask and heated at reflux one hour then stripped under reduced pressure.

The residue was extracted with dichloromethane, filtered through dicalite and stripped under reduced pressure to yield the desired product. Structure was confirmed by infrared, and proton nuclear magnetic resonance.

EXAMPLE 6

Preparation of N-phosphonomethylglcyine

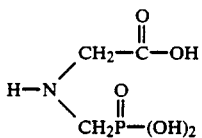

9.85 g (0.0326 mole) of O,O-diethyl-N-cyanomethyl-N-trifluoroacetylaminomethyl phosphonate were combined with 50 ml (0.6 mole) of concentrated hydrochloric acid in a round bottom flask, heated at reflux 1.5 hours, and stripped under reduced pressure to yield the desired product. Structure was confirmed by infrared, proton nuclear magnetic resonacne and $C^{13}$ spectroscopy.

I claim:

1. A method of preparing N-phosphonomethylglycine comprising (a) reacting at a temperature ranging from about 0° to about 100° C. and at a pressure ranging from subatmospheric to superatmospheric, an N-hydroxymethyl haloacetamide of the formula

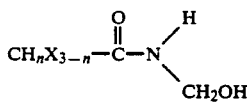

wherein X is chlorine, bromine or fluorine and n is an integer from 0 or 1 with a chlorinating agent to form an N-chloromethyl haloacetamide which has the structural formula

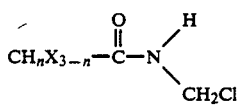

wherein X and n are as defined above;

(b) reacting at a temperature ranging from about 0° to about 150° C., the haloacetamide formed in step (a) with a phosphite of the formula

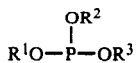

wherein $R^1$ and $R^2$ are both aromatic groups or both aliphatic groups, and $R^3$ is an aliphatic group, to form a phosphonate compound of the formula

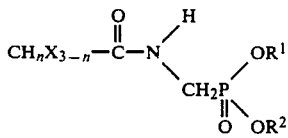

wherein n, X, $R^1$ and $R^2$ are as defined:

(c) reacting at a temperature ranging from about 0° to about 150° C. and at a pressure ranging from substmospheric to superatmospheric, the phosphonate of step (b) with a compound of the structural formula in the presence of a non-nucleophilic base

Y—CH₂—Z wherein Y is chlorine, bromine or iodine and Z is cyano or

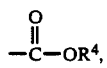

$R^4$ being an aromatic of aliphatic group to form a phosphonate compound of the formula

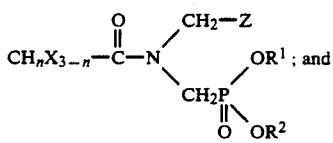

(d) hydrolyzing at a temperature ranging from about 0° to about 200° C. and at a pressure ranging from subatmospheric to superatmospheric, the phosphonate formed in step (c) to yield N-phosphonomethylglycine.

2. The method of claim 1 wherein X is fluorine and n is the integer 0.

3. The method of claim 1 wherein $R^1$ is $C_1$-$C_6$ alkyl, $R^2$ is $C_1$-$C_6$ alkyl, $R^3$ is $C_1$-$C_6$ alkyl, $R^4$ is $C_1$-$C_4$ alkyl and X is chlorine.

4. The method of claim 1 wherein $R^1$ is $C_1$-$C_4$ alkyl, $R^2$ is $C_1$-$C_4$ alkyl, $R^3$ is $C_1$-$C_4$ alkyl, $R^4$ is $C_1$-$C_4$ alkyl, X is chlorine and n is the integer 0.

5. The method of claim 1 wherein $R^1$ is $C_1$-$C_2$ alkyl, $R^2$ is $C_1$-$C_2$ alkyl, $R^3$ is $C_1$-$C_2$ alkyl, $R^4$ is $C_1$-$C_2$ alkyl, X is fluorine and n is the integer 0.

6. The method of claim 1 wherein R, $R^1$, $R^2$ and $R^3$ are methyl and X is chlorine.

7. The method of claim 1 wherein step (a) is run at a temperature between about 40° to about 100° C.

8. The method of claim 7 wherein step (d) is done with an acid catalyst.

9. The method of claim 8 wherein the acid catalyst is hydrochloric or hydrobromic acid.

* * * * *